United States Patent
Schipper et al.

(12) 
(10) Patent No.: US 6,210,895 B1
(45) Date of Patent: Apr. 3, 2001

(54) HO-1 AS A DIAGNOSTIC AND PROGNOSTIC TEST FOR DEMENTING DISEASES

(75) Inventors: Hyman M. Schipper, 5785 Einstein, Montreal, Quebec (CA), H4W 2Y9; Howard Chertkow, 355 Landsdowne Avenue, Westmount, Quebec (CA), H3Z 2L5

(73) Assignees: The Sir Mortimer B. Davis-Jewish General Hospital; Hyman M. Schipper; Howard Chertkow, all of (CA)

( * ) Notice: Subject to any disclaimer, the term of this patent is extended or adjusted under 35 U.S.C. 154(b) by 0 days.

(21) Appl. No.: 09/323,248

(22) Filed: Jun. 1, 1999

Related U.S. Application Data (60) Provisional application No. 60/098,141, filed on Aug. 27, 1998.

(30) Foreign Application Priority Data

| | | |
|---|---|---|
| Jun. 1, 1998 | (CA) | 2239281 |
| Apr. 19, 1999 | (CA) | 2269432 |

(51) Int. Cl.⁷ ............................ C12Q 1/68; C12Q 1/26; C12N 9/02
(52) U.S. Cl. .................. 435/6; 435/25; 435/189
(58) Field of Search .................. 435/6, 25, 189

(56) References Cited

FOREIGN PATENT DOCUMENTS 2222174  6/1996 (CA).

OTHER PUBLICATIONS

Grossi et al , Clinical and behavioral variants of Alzheimer type dementias, II International Symposium, Eds, Paris 1988.
Schipper et al., Evaluation of heme oxygenase–1 as a systemic biological marker of sporadic AD, Neurology, 1297–1304, 2000.
Chomczynski P and Sacchi N. (1987) Single–step method of RNA isolation by acid guanidinium thiocyanate–phenol–chlorophorm extraction. Analytical Biochem 162:156–159.
Church GM and Gilbert W. (1984) Genomic sequencing. Proc Nat Aca Sci USA 81:1991–1995.
Feinberg AP and Vogelstein B. (1984) A technique for radioabelling DNA restriction endonuclease fragments to high specific activity. Analytical Biochem 137:266–267.
Grossi, D., et al. (1988) Senile dementias. II International Symposium (pp. 97–99). Paris: John Libbey Eurotext.
Haxby JV, et al. (1992) Individual trajectories of cognitive declline in patients with dementia of the Alzheimer type. J Clin Exp Neuropsychol 14:575–592. Abstract.
Mann, U., (1992) Heterogeneity in Alzheimer's disease: Progression rate segregated by distinct neuropsychological and cerebral metabolic profiles. J Neurol Neurosurg Phychiatry 55:956–959.
Noonberg SB, et al. *1994) Detection of triplex–forming RNA oligonucleotides by triplex blotting. BioTechniques 16:1070–1072.
Schipper HM, et al. (1995) Expression of heme oxygenase–1 in the senescent and Alzheimer–diseased brain. Ann Neurol 37:758–768.
Wang, G.P., et al. (1991) Alzheimer's disease: paired helical filament immunoreactivity in cerebrospinal fluid. Acta Neuropathol 82:6–12.
Schipper HM, et al. (1997) Blood Heme Oxygenase–1 Levels are Decreased in Alzheimer's Disease, Soc. Neuroscience 23:1641 (Abs. 637.10).
Schipper HM, et al. (1999) Further Evaluation of Heme Oxygenase–1 as a Biological Marker in Alzheimer's Disease, Neurology. 52:A126 (Suppl. 2) (Abs. P02.032).
Premkumar et al., J. Nuerochemistry, 65(3), 1399–1402, Aug. 1995.*
Keyse et al., PNAS USA, 86, 99–103, Jan. 1989.*
Dorland's medical Dictionary, 27th edition, W.B. Saunders, p. 1725, 1985.*

* cited by examiner

*Primary Examiner*—Rebecca E. Prouty
*Assistant Examiner*—M. Monshipouri
(74) *Attorney, Agent, or Firm*—Lorusso & Loud

(57) ABSTRACT

The invention relates to a method for predicting the onset of, diagnosing, and/or prognosticating dementing diseases. The method comprises determining the concentration of heme oxygenase-1 (HO-1) and/or a nucleotide sequence encoding HO-1 in tissue obtained from a patient, and comparing said concentration with the corresponding concentration of HO-1 and/or an HO-1 encoding nucleotide sequence in corresponding tissue obtained from at least one control person. The tissue is suitably plasma, lymphocytes, cerebrospinal fluid or fibroblasts. The method is useful where the dementing disease is any of Alzheimer's Disease, Age-Associated Cognitive Decline, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, Creutzfeld-Jacob disease, viral encephalitis and hypothyroidism.

8 Claims, 7 Drawing Sheets

HO-1 AS A DIAGNOSTIC AND PROGNOSTIC TEST FOR DEMENTING DISEASES

This application claims the benefit of U.S. Provisional Application No. 60/098,141, filed Aug. 27, 1998.

FIELD OF THE INVENTION

This invention relates to a method for predicting, diagnosing, and prognosticating dementing diseases such as Alzheimer's Disease (AD) and Age-Associated Cognitive Decline (AACD).

BACKGROUND OF THE INVENTION

Alzheimer's Disease is a neurodegenerative disease which causes dementia. The period from first detection of AD to termination can range from a few years to 15 years, during which time the patient progressively suffers loss of both mental function and control of bodily functions. There is significant variability in the progress of the disease. While the majority of patients have a gradual, inexorable progression (losing on average 3 to 4 points on the 30 point Folstein mini-mental state score annually), approximately 30% of AD cases have a prolonged stable initial plateau phase lasting several years (Haxby et al., 1992). A subgroup of patients has a fulminant, rapidly progressive downhill course over several years (Mann et al., 1992). Other patients (about 10% of cohorts) remain slowly progressive, showing only gradual decline from year to year (Grossi et al., 1988). The pathological, chemical, and molecular bases of this heterogeneity remain undetermined. Recognition of the variability of AD progression represents an important clinical insight, and may explain the diagnostic difficulties presented by "atypical" cases.

Attempts at predicting the onset of AD or monitoring its progression have met with limited success. While in certain cases, there is a familial manifestation of the disease, it appears that the majority of AD cases are non-familial, and no simple genetic marker for the disease has yet been determined. Much research has focused on the protein beta-amyloid, deposits of which are found in the brains of AD victims.

Methods of predicting, diagnosing in its very early stage, and prognosticating AD and other dementing diseases are needed.

SUMMARY OF THE INVENTION

It is a goal of the present invention to provide a method for predicting, diagnosing, and prognosticating AD and other dementing diseases.

In one embodiment, the invention provides a method for assessing dementing diseases in a patient which comprises determining the concentration of heme oxygenase-1 (HO-1) and/or a nucleotide sequence encoding HO-1, in tissues obtained from a patient, and comparing said concentration with the corresponding concentration of HO-1 and/or an HO-1 encoding nucleotide sequence in corresponding tissues obtained from at least one control person, wherein such method is used to predict the onset of, diagnose, or prognosticate dementing diseases.

In another embodiment, the invention provides a commercial package comprising means for determining the concentration of heme oxygenase-1 (HO-1) and/or a nucleotide sequence encoding HO-1, in tissues obtained from a patient, and instructions for comparing said concentration with an established standard of the corresponding concentration of HO-1 and/or an HO-1 encoding nucleotide sequence in corresponding tissues obtained from at least one normal age-matched control person or from the patient at an earlier time.

The tissues to which the method can be applied include plasma, cerebrospinal fluid, lymphocytes and fibroblasts.

Advantageously, embodiments of this invention provide an easily administered blood or cerebrospinal fluid test which is used to predict, diagnose, or prognosticate AD and other dementing diseases.

BRIEF DESCRIPTION OF THE DRAWINGS

FIG. 5 is a graph showing HO-1 levels as a function of rate of decline in AD. The rate of global deterioration (x-axis) was derived using the difference between two successive Folstein mini-mental scores, multiplied by 3, divided by the intervening months. Those with more rapid decline (x>1) were associated with the most decreased HO-1 levels.

DESCRIPTION OF THE EMBODIMENTS OF THE INVENTION

The Applicant has devised a diagnostic method, potentially useful in the prediction, diagnosis, and prognostication of AD, AACD, and related neurological diseases. This diagnostic method is based on the discovery that patients suffering from AD have a significantly lower concentration of heme oxygenase-1 (HO-1) in their lymphocytes and plasma, and, accordingly, a significantly lower concentration of nucleotide sequences encoding HO-1 in their lymphocytes.

HO-1: Heme oxygenase-1 (HO-1) is an enzyme that catalyses the rapid degradation of heme to biliverdin in brain and other tissues. This 32 kDa member of the heat shock protein superfamily contains a heat-shock element in its promoter region and is rapidly up regulated in response to oxidative stress, metal ions, amino acid analogues, sulfhydryl agents, and hyperthermia. In response to oxidative stress, induction of HO-1 may result in protection of cells by catabolizing pro-oxidant metalloporphyrins, such as heme, into bile pigments (biliverdin, bilirubin), with free radical scavenging capabilities. Heme and other intracellular ferrous iron chelates are capable of converting hydrogen peroxide to the highly cytotoxic hydroxyl radical.

Using immunostaining techniques in conjunction with laser scanning confocal microscopy, intense HO-1 immunoreactivity in neurons and astrocytes of post-mortem hippocampus and temporal cortex derived from AD subjects has been observed, whereas neural HO-1 staining was faint or non-existent in the hippocampus and temporal cortex of control specimens matched for age and post-mortem interval (Schipper et al., 1995). Furthermore, consistent co-localization of HO-1 to neurofibrillary tangles and senile plaques in the AD specimens has been demonstrated. Finally, robust 32 kDa bands corresponding to HO-1 were observed by Western blotting of protein extracts derived from AD temporal cortex and hippocampus after SDS-PAGE, whereas control HO-1 bands were faint or absent. These results indicate that HO-1 is significantly overexpressed in neurons and astrocytes of AD hippocampus and cerebral cortex relative to control brains and support the contention that AD-affected tissues are experiencing chronic oxidative stress.

AACD: AACD is a term used to identify individuals who experience a cognitive decline that falls short of dementia. Satisfaction of criteria (World Health Organization) for this diagnosis requires a report by the individual or family of a decline in cognitive function, which is gradual, and present at least 6 months. There may be difficulties across any cognitive domains (although memory is impaired in rag the vast majority of cases), and these must be supported by abnormal performance on quantitative cognitive assessments for which age and education norms are available for relatively healthy individuals (ie., the patient is compared to normal subjects his/her own age). Performance must be at least 1 SD below the mean value for the appropriate population on such tests. Neither dementia, nor significant depression or drug effects may be present. No cerebral or systemic disease or condition known to cause cerebral cognitive dysfunction may be present. In the Applicant's experience, all patients who were classified as CDR.5 ("questionable dementia") on the Clinical Dementia rating Scale and who met these exclusions, also met the criteria for AACD.

About 1/3 of Alzheimer's patients have had a clearly definable period of isolated memory deficit which preceded their more global cognitive decline (Haxby et al., 1992). Using AACD criteria which look at other domains in addition to memory, the percentage with an identifiable prodrome is likely higher. Fortunately, not all AACD individuals seem to decline. It appears that a significant number of these subjects show a stable, non-progressive memory deficit on testing.

Related Disorders: Determining HO-1 concentration can also assist in predicting, diagnosing, or prognosticating other dementing diseases having similar manifestations and/or in distinguishing such diseases from AD. Such other diseases include Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, Creutzfeld-Jacob disease, viral encephalitis and hypothyroidism.

EXAMPLE 1

Determination of Blood HO-1 Levels

Whole blood is collected from subjects in heparinized tubes. This is then layered over a Ficol Paque density gradient and centrifuged at 1800 rpm for 20 minutes. The top plasma layer is then collected and saved for ELISA after addition of Complete™ protease inhibitor cocktail (Boehringer Mannheim).

Lymphocyte crude microsomal fraction: The layer of Ficol Paque gradient containing lymphocytes is collected and washed three times in PBS and centrifuged at 3500 rpm for 10 minutes. The resulting pellet is stored in Cell Culture Freezing Medium-DMSO (Gibco). After thawing, the pellet is washed three times in PBS and spun at 3000 rpm for 10 minutes. The resulting pellet is resuspended in 100 $\mu$l 5 mM EDTA, 10 mM Tris and 150 mM NaCl pH 7.4 to lyse the cells. Lysate is homogenized and centrifuged at 100,000 rpm for 50 minutes to pack down membrane fraction. Pellet is then solubilized with Triton-X100 and Tris pH 7.4.

HO-1 protein and HO-1 antibody (StressGen, Victoria BC) are used to measure the percent competitive inhibition of HO-1 protein in human plasma and lymphocytes. Alkaline phosphatase conjugated IgG (Bio Can) with p-nitrophenyl phosphate disodium (Sigma) as substrate is used to visualize the reaction.

ELISA: Competitive ELISA for the detection and quantification of HO-1 is performed according to the procedure of Wang et al. (1991) with the following modifications: Immulon II ELISA plates (Dynatech) are coated (50 $\mu$l/well) with 0.5 $\mu$g/ml HO-1 protein (dissolved in coating buffer containing $Na_2CO_3$ and $NaHCO_3$ pH 9.6) and incubated overnight at 4° C. Excess protein is then washed off with washing buffer containing Tris, NaCl and Tween-20. Wells are blocked with 3% bovine serum albumen (BSA) in coating buffer and incubated 2 hrs at 37° C. 75 $\mu$l of plasma or solubilized membrane is then mixed with 75 $\mu$l of HO-1 antibody (diluted 1/50,000) and incubated for 2 hrs. at room temperature. After blocking, wells are washed with 50 $\mu$l/well of plasma or solubilized membrane and HO-1 antibody mixture is added and incubated overnight at 40° C. Any available antibody combines with the antigen exposed on the coated well. Secondary antibody consisting of alkaline phosphatase conjugated IgG anti-rabbit (diluted 1/1000) in 0.1% BSA is added and incubated 2 hrs at 37° C. 50 $\mu$l of the substrate (p-nitrophenyl phosphate disodium dissolved in diethanolamine pH 9.8) is added to each well and incubated for 20 minutes at room temperature. The resulting colour reaction is read at 405 nm wavelength on a multi-well scanning spectrophotometer (Molecular Devices Corp.). The standard curve consists of equal volumes of HO-1 protein (10, 5.0, 2.5, 1.0, 0.5, 0.1 $\mu$g/ml) and HO-1 antibody (1/50,000) which are mixed and incubated for 2 hrs at room temperature. This mixture is then added to the protein coated, BSA blocked wells in the same manner as test samples. The results of % maximum inhibition are calculated based on the standard curve generated by the known amounts of HO-1 proteins in the standard samples.

EXAMPLE 2

Comparison of Blood HO-1 Levels Among Individuals with Varying Degrees of Dementia HO-1 levels in plasma and lymphocytes were assessed in normal elderly controls (NEC), patients probably with Alzheimer's Disease (AD) diagnosed according to NINCDS criteria, individuals with age-associated cognitive decline not meeting AD criteria (AACD), and subjects with other neurological and medical disorders (Schipper et al., 1997; Schipper et al., in press). Demographic data is summarized in Table 1.

Figure 1:
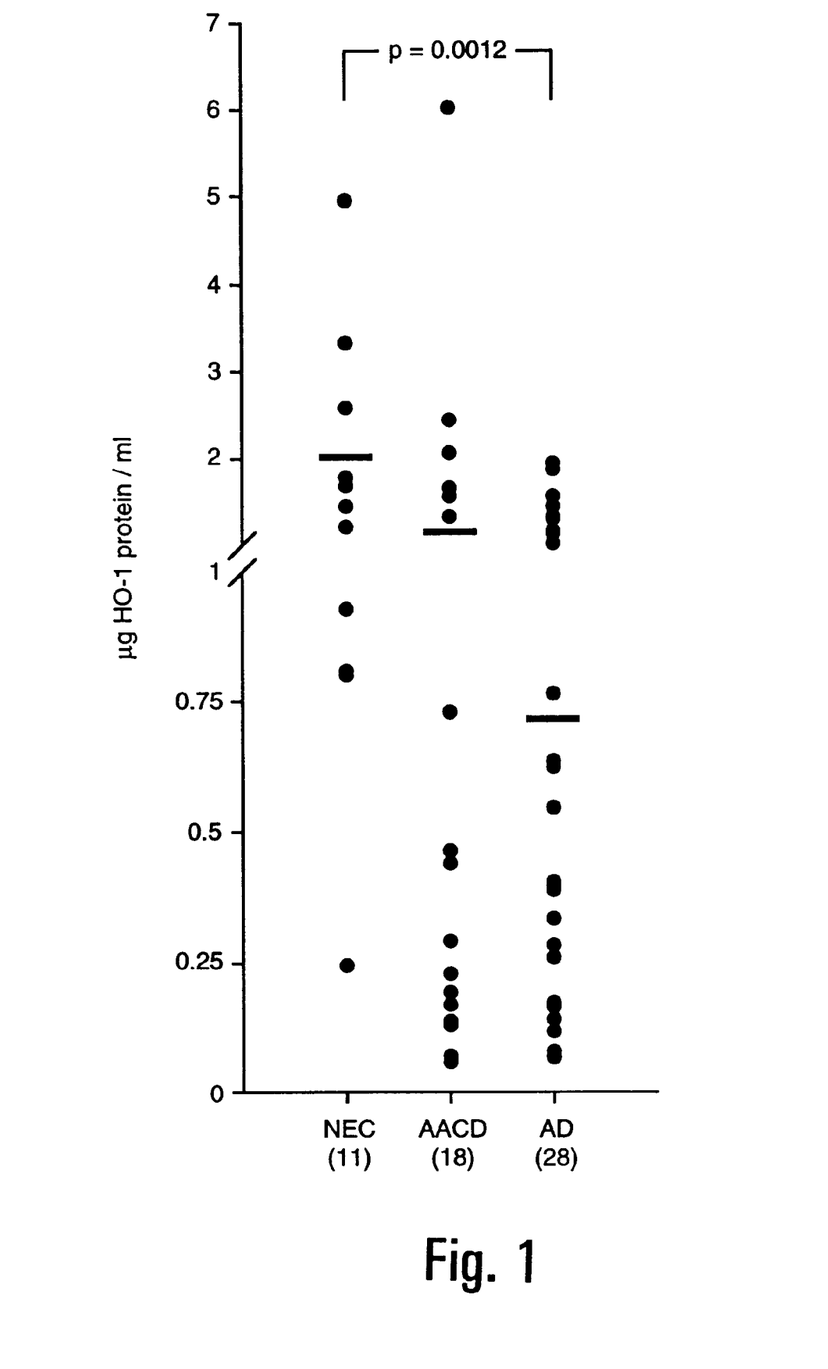
FIG. 1 is a graph showing results from a competitive HO-1 ELISA on plasma from subjects, by group. AD group had significantly decreased heme oxygenase-1 (HO-1) levels. No controls had a level below 1.0 $\mu$g/ml. Mean values are indicated by the horizontal bars and statistically significant differences between groups are indicated on the graph.
Figure 2:
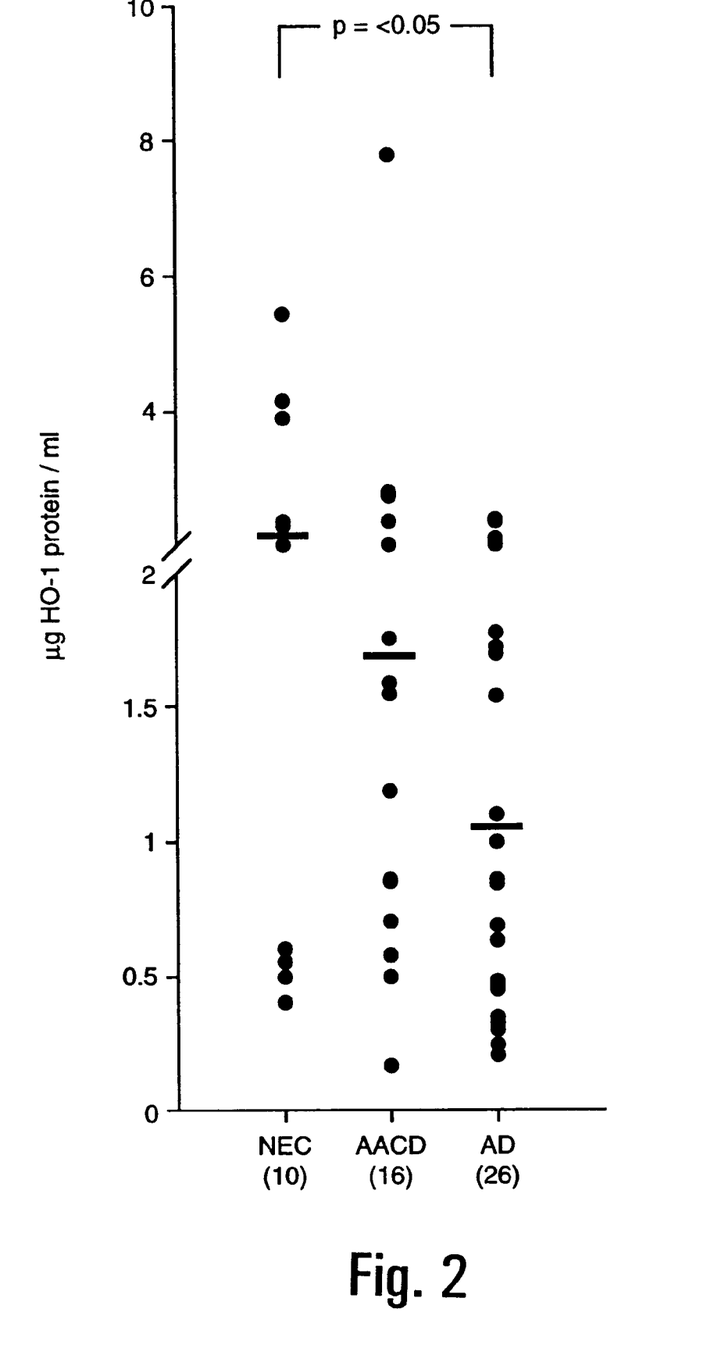
FIG. 2 is a graph showing results from a competitive HO-1 ELISA on lymphocytes from subjects, by group. AD group had significantly decreased heme oxygenase-1 (HO-1) levels. No controls had a level below 1.0 $\mu$g/ml. Mean values are indicated by the horizontal bars and statistically significant differences between groups are indicated on the graph.
Figure 3:
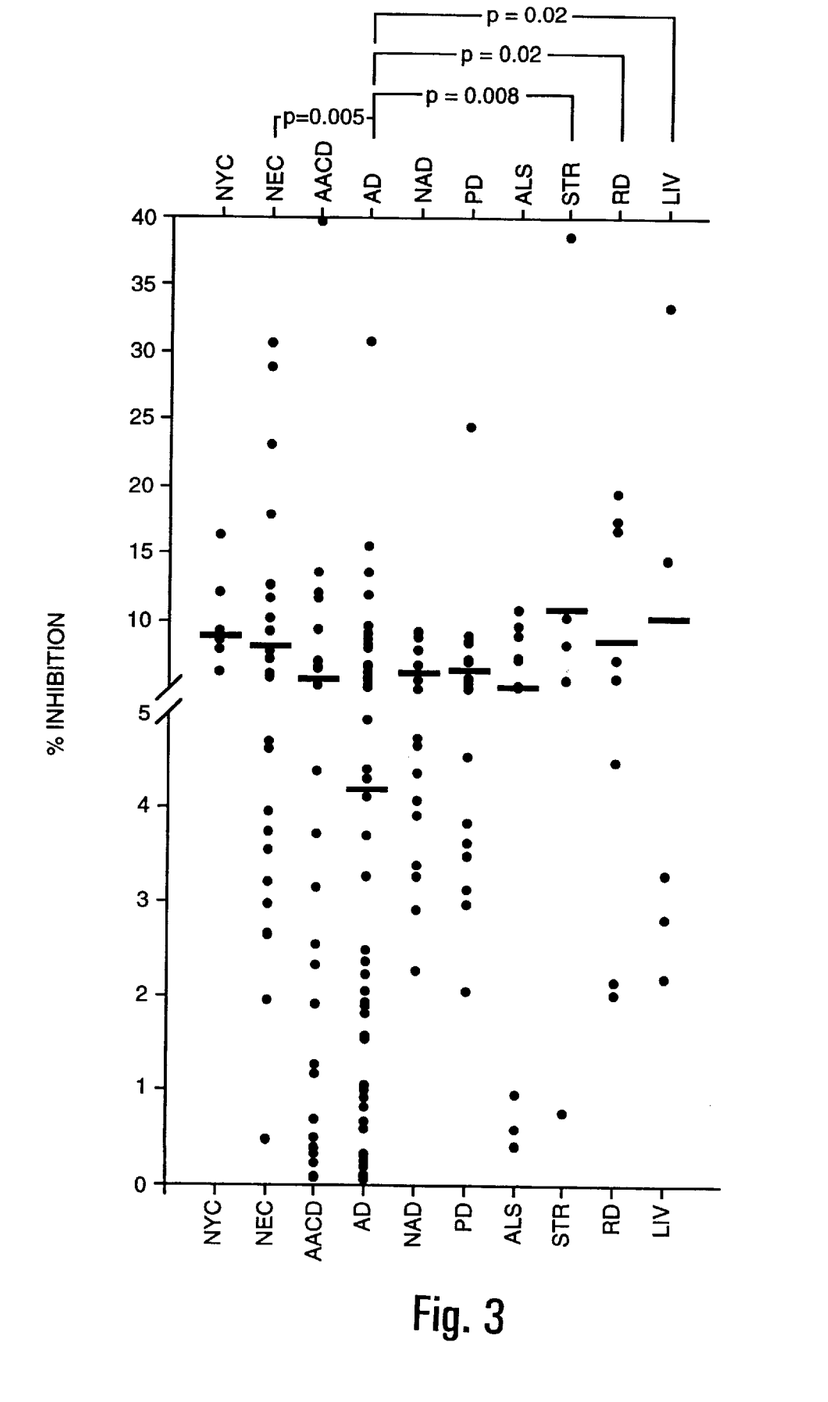
FIG. 3 is a graph showing results from a competitive HO-1 ELISA on plasma from subjects, by group, measured as % maximum inhibition, which is directly proportional to protein concentrations. AD group had significantly decreased % inhibition and therefore of heme oxygenase-1 (HO-1) levels. Mean values are indicated by the horizontal bars and statistically significant differences between groups are indicated on the graph.

A competitive ELISA was used to determine HO-1 levels in plasma and blood lymphocytes. In an early study (Schipper et al., 1997), Applicant found that mean plasma and lymphocyte concentrations of HO-1 were significantly lower in AD subjects than in normal controls. For plasma, the AD subjects had mean 0.715+/−0.113 µg/ml, vs 1.8+/−0.41 µg/ml for controls. This difference was highly significant (p=0.0012). For lymphocytes, the AD subjects had HO-1 levels of 1.16+/−0.15 µg/ml, vs 2.23+/−0.56 µg/ml for controls, again demonstrating a significant difference (p<0.05). The AACD group overall demonstrated levels midway between the two other groups: mean 1.01+/−0.35 µg/ml for plasma, and mean 1.76+/−0.46 µg/ml for lymphocytes. Subsequent studies (Schipper et al., in press) confirmed these results. See FIGS. 1, 2 and 3.

Figure 4:
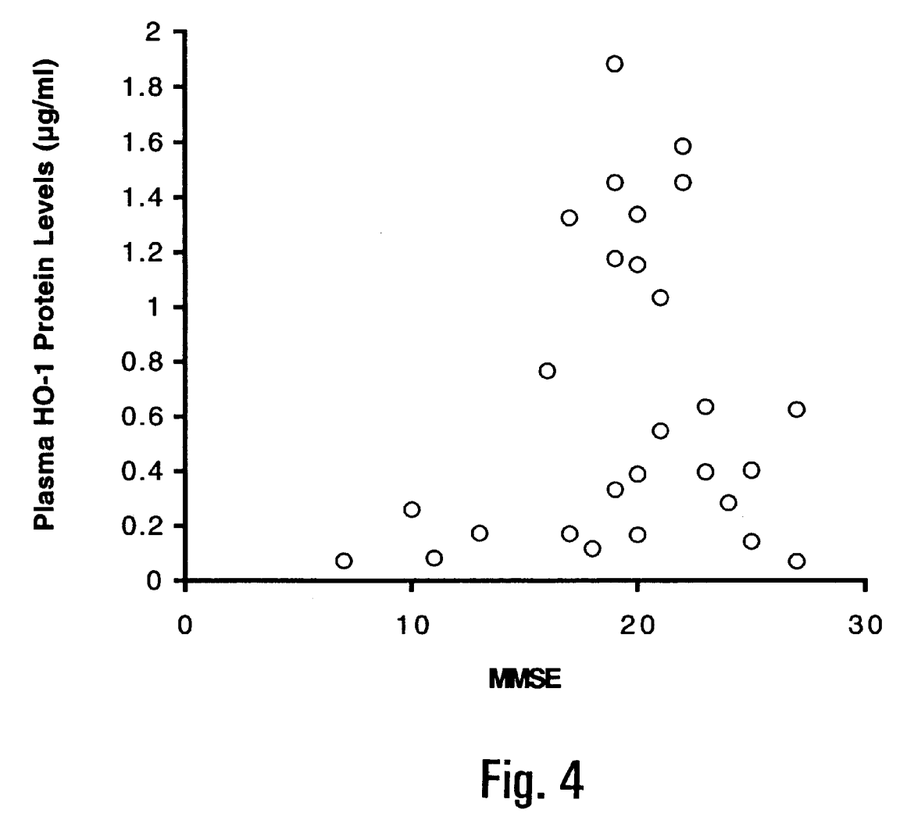
FIG. 4 is a graph showing HO-1 levels as a function of Folstein MMSE scores in AD. Those with more severe dementia (lower MMSE) were associated with decreased HO-1 levels.

While there does exist overlap in scores between the groups, cut-off levels can be established (eg., 1.0 µg/ml) below which no normal subjects exist, but below which lie 25% of AD subjects, and also 25% of AACD subjects. Presumably, any AACD subject lying in this range would have a high (or perhaps even a certain) chance of progressing to AD over longitudinal follow-up. In addition, analysis of the clinical data on these subjects revealed important correlations. There was no correlation between HO-1 levels and age or duration of symptoms. There was, however, a significant correlation between HO-1 serum levels, and the Folstein Mini-mental state level, a general measure of dementia severity (r=0.57, p<0.005) (see FIG. 4). This suggests that as the AD subjects became more severely demented, their HO-1 levels progressively decrease.

Figure 5:
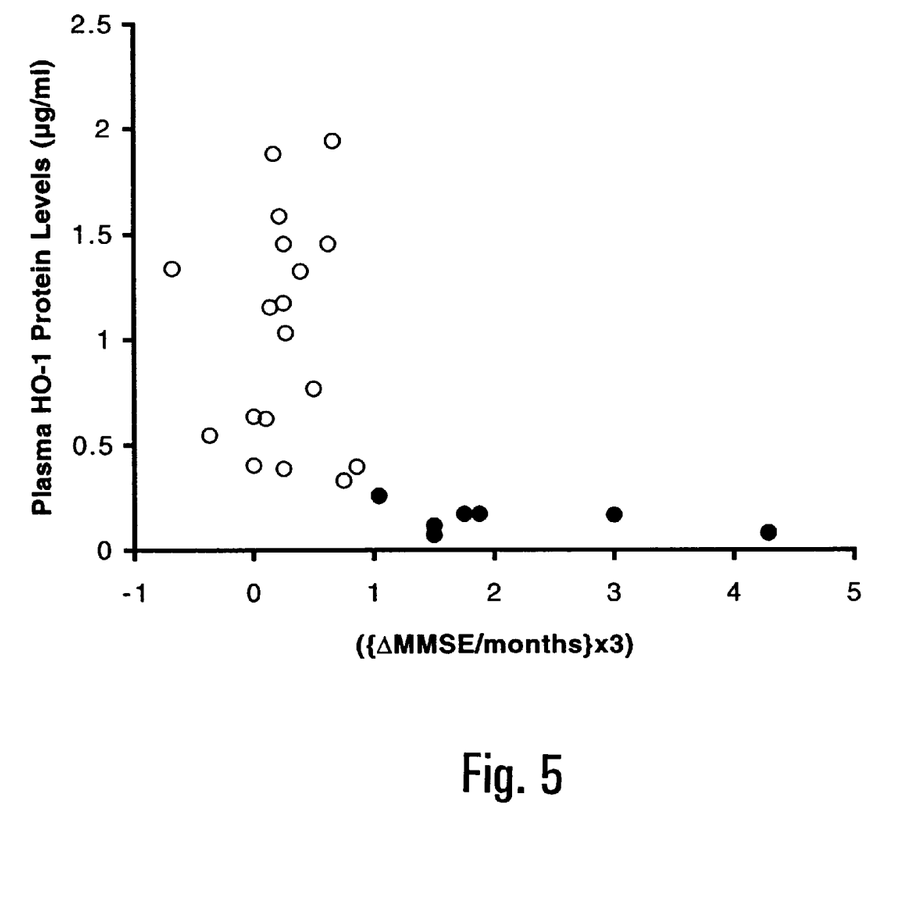

Further analysis, however, suggests an alternative explanation. It was noted in the study that the most severely demented patients also seemed to be those who had deteriorated most rapidly. A measure of rate of global deterioration was derived (the difference between two successive Folstein Mini-mental scores, multiplied by 3, divided by the intervening months). This formula was derived in view of the Applicant's past experience that the typical AD subject declines by 3 or 4 points on the MMSE per year. The association between rate of decline and HO-1 levels was the most robust of all (r=−0.72, p<0.0001) (see FIG. 5). The implication is that the patients showing the most rapid decline demonstrated the lowest levels of HO-1. Accordingly, HO-1 serum levels offer the possibility of producing useful prognostic information; the presence of a low HO-1 level would imply more rapid deterioration over time in AD subjects. The method can, accordingly, usefully be used to compare HO-1 levels in the same patient over time in order to prognosticate the disease.

EXAMPLE 3

Comparison of Lymphocyte HO-1 mRNA Levels Among Individuals with Varying Degrees of Dementia Lymphocyte HO-1 mRNA levels were determined by Northern analysis in normal elderly controls (NEC), patients probably with Alzheimer's Disease (AD) diagnosed according to NINCDS criteria, individuals with age-associated cognitive decline not meeting AD criteria (AACD), and subjects with other neurological and medical disorders (Schipper et al., 1997; Schipper et al., in press) derived from the same sources and diagnosed according to the same criteria as described in Example 2 above.

Lymphocyte fractions were obtained by differential centrifugation of whole blood on Ficol Paque gradients as described above. Cytoplasmic RNA was isolated from the lymphocytes using an acid guanidinium thiocyanate-phenol-chloroform extraction method (Chomezynski P et al., 1997). Six micrograms of RNA was denatured and size-separated by electrophoresis on 1% agarose/formaldehyde gels. RNA integrity was confirmed by ethidium bromide staining. The RNA was transferred onto Hybond-N filter paper and covalently cross-linked to the membrane by UV light for two minutes. The hybridization probe (HO-1; 1.0 kb) was prepared by random priming using the Random Primer DNA Labelling System (Feinberg AP et al., 1984). Prehybridization was performed for 12 hours at 42° C. in a buffer containing formamide deionized, 5×Denhardt's reagent, 6×SSPE and 0.5% SDS. The hybridization buffer consisted of the prehybridization buffer without 5×Denhardt's reagent, and $^{32}$P-labelled denatured DNA probe (Noonberg SB et al., 1994). Equal loading of RNA was confirmed by hybridization with a cDNA for the (housekeeping) gene, glyceraldehyde-3-phosphate dehydrogenase (GAPDH). All washes were performed under stringent conditions (1×SSC and 0.2% SDS for 45 minutes at room temperature, 0.4×SSC and 0.2% SDS for 15 minutes at 65° C.). The RNA hybridizing with cDNA probes was visualized by autoradiography using an intensifying screen at −80° C. (Church G M et al., 1984).

Figure 6:
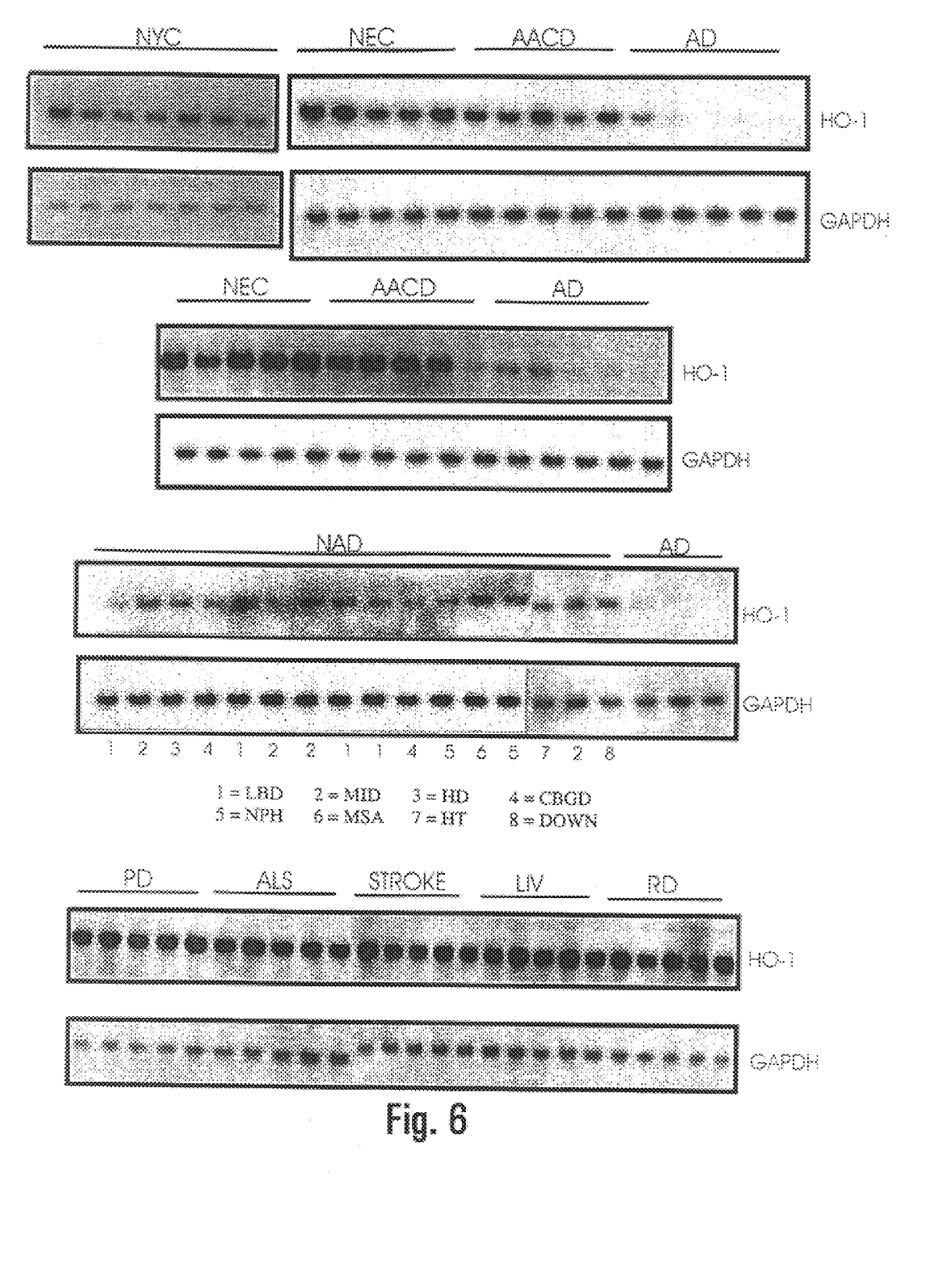
FIG. 6 is a Northern analysis of HO-1 mRNA levels in lymphocytes derived from subjects with Alzheimer's disease (AD), age-associated cognitive decline (AACD) and normal elderly controls (NEC), etc. as described in Example 3. Control GAPDH bands used to ensure uniformity of RNA loading are depicted below the HO-1 bands.
Figure 7:
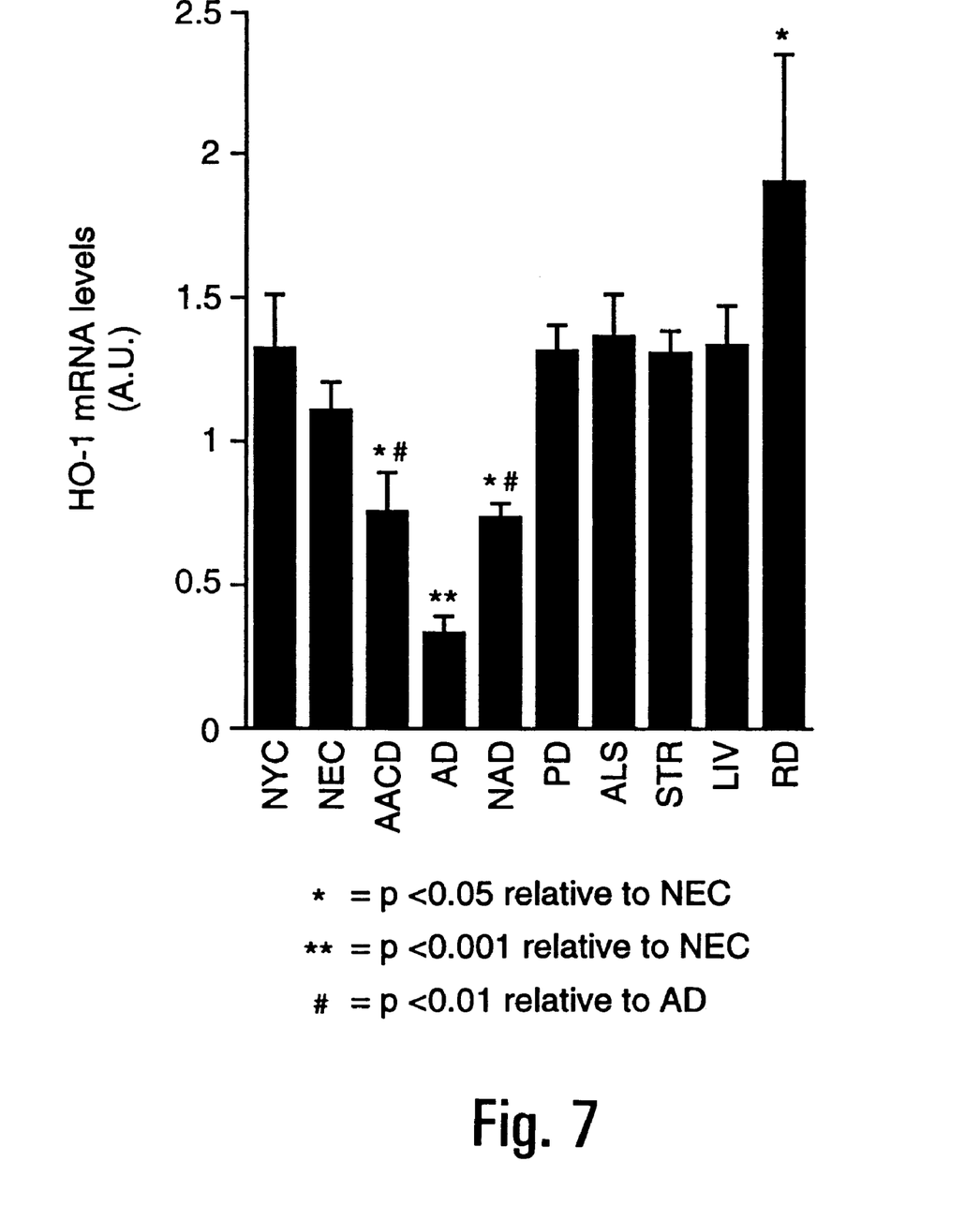
FIG. 7 is a graph showing results from a Northern analysis of HO-1 mRNA levels in lymphocytes derived from the subjects described in Example 3. AD group had significantly decreased heme oxygenase-1 (HO-1) mRNA levels.

Lymphocyte HO-1 mRNA bands, assayed by Northern analysis, were uniformly robust in the NEC subjects. In contrast, HO-1 mRNA bands were faint or undetectable in lymphocytes derived from AD subjects and of variable intensity in the AACD cohort (see FIG. 6). Quantification by densitometry produced the results in FIG. 7.

The above examples illustrate the testing method using blood and lymphocytes as the tissue samples. The method can also be applied to other tissues such as cerebrospinal fluid and to fibroblast cell lines derived from patients.

The examples also illustrate application of the testing method to detect concentration of HO-1 as well as of HO-1 mRNA.

The test can be applied to compare the concentration of HO-1 or a nucleotide sequence encoding it in a specific patient over a period of time, or to compare the concentration of HO-1 or a nucleotide sequence encoding it in a patient with the corresponding concentration in a normal control population.

A kit or commercial package for carrying out the testing method includes a means for determining the concentration of heme oxygenase-1 (HO-1) and/or a nucleotide sequence encoding HO-1, in tissue obtained from a patient. It also includes instructions for comparing said concentration with an established standard of the corresponding concentration of HO-1 and/or an HO-1 encoding nucleotide sequence in corresponding tissue obtained from at least one normal elderly control person or from the patient at another time.

TABLE 1

| DIAGNOSIS | n | AGE (mean) | SEX F/M | MMSE (mean) | EDUC. (mean) |
|---|---|---|---|---|---|
| CONTROL | 31 | 62.5 | 17/14 | 29.4 | 14.1 |
| Age 40–60 (NYC)⊕ | 7 | 47.1 | 1/6 | 30 | 16.6 |
| 60+ (NEC)* | 24 | 77.9 | 16/8 | 28.9 | 11.7 |
| AACD* | 25 | 76.3 | 15/10 | 26.9 | 10.5 |
| AD* | 50 | 76.8 | 27/23 | 21.1 | 10.9 |
| NAD*♦ | 16 | 74.3 | 6/9 | 11.5 | — |
| LBD | 4 | 71.25 | 2/2 | 18.2 | — |

TABLE 1-continued

| DIAGNOSIS | n | AGE (mean) | SEX F/M | MMSE (mean) | EDUC. (mean) |
|---|---|---|---|---|---|
| CBGD | 2 | 69.6 | 1/1 | 7.5 | — |
| HD | 1 | 63 | M | 24 | |
| NPH | 2 | 81.0 | 2M | 25 | — |
| MID | 4 | 77.5 | 1/3 | 6.2 | — |
| MSA | 1 | 86 | M | 11 | — |
| DOWN | 1 | 55 | F | 0 | — |
| HT | 1 | 86 | F | 0 | — |
| PD • | 21 | 68.7 | 10/11 | 29.0 | — |
| ALS ∆ | 14 | 55.7 | 8/6 | 28.9 | — |
| SALS | 13 | 56.1 | 8/5 | 28.8 | — |
| FALS | 1 | 50 | M | 30 | — |
| STR # | 5 | 61.8 | 1/4 | 26 | — |
| RD♣ | 8 | 63.4 | 6/2 | 27.6 | — |
| LIV♣ | 5 | 51.8 | 2/3 | 27.2 | — |
| HS | 4 | 51.0 | 2/2 | 26.5 | — |
| CAH | 1 | 55 | M | 30 | — |

AACD = age-associated cognitive decline
AD = Alzheimer disease
ALS = amyotrophic lateral sclerosis
CAH = chronic active hapatitis (A/B)
CBGD = coritcobasal ganglionic degeneration
DOWN = Down syndrome
EDUC = years of formal education
FALS = familial amyotrophic lateral sclerosis
HD = Huntington disease
HS = hepatic steatosis
HT = head trauma
LBD = Lewy body dementia
LIV = liver diseases
MID = multi-infarct dementia
MSA = multi system atrophy
NAD = Non-Alzheimer dementia
NEC = normal elderly controls
NPH = normal pressure hydrocephalus
PD = Parkinson disease (non-demented)
RD = rheumatic diseases
SALS = sporadic amyotrophic lateral sclerosis
STR = stroke (cerebral infarction)
Subjects recruited from:
⊕ sectors of the Montreal community serviced by the Jewish General Hospital (JGH).
*McGill Memory Clinic (JGH); groups did not differ significantly in age or formal education.
♦ Maimonides Chronic Care Hospital (Montreal)
• JGH Movement Disorder Clinic
∆ ALS Society of Montreal
JGH outpatients
♣ JGH Liver and Rheumatic Diseases Clinics

REFERENCES

Chomczynski P and Sacchi N. (1987) Single-step method of RNA isolation by acid guanidinium thiocyanate-phenol-chlorophorm extraction. Analytical Biochem 162:156–159.

Church G M and Gilbert W. (1984) Genomic sequencing. Proc Nat Aca Sci USA 81:1991–1995.

Feinberg A P and Vogelstein B. (1984) A Technique for radiolabelling DNA restriction endonuclease fragments to high specific activity. Analytical Biochem 137:266–267.

Grossi, D., et al. (1988) Senile dementias. II International Symposium (pp. 97–99). Paris: John Libbey Eurotext.

Haxby J V, et al. (1992) Individual trajectories of cognitive decline in patients with dementia of the Alzheimer type. J Clin Exp Neuropsychol 14:575–592.

Mann, U., et al. (1992) Heterogeneity in Alzheimer's disease: Progression rate segregated by distinct neuropsychological and cerebral metabolic profiles. J Neurol Neurosurg Psychiatry 55:956–959.

Noonberg S B, et al. (1994) Detection of triplex-forming RNA oligonucleotides by triplex blotting. BioTechniques 16:1070–1072.

Schipper H M, et al. (1995). Expression of heme oxygenase-1 in the senescent and Alzheimer-diseased brain. Ann Neurol 37:758–768.

Schipper H M, et al. (1997) Blood Heme Oxygenase Levels are decreased in Alzheimer's disease. Proc Soc for Neuroscience 123:1–41.

Schipper H M, et al. (in press) Blood Heme Oxygenase-1 Levels are Decreased in Alzheimer's Disease and Correlate Inversely with Rates of Disease Progression.

Schipper H M, et al. (in press) Further Evaluation of Heme Oxygenase-1 as a Biological Marker in Alzheimer's Disease.

Wang, G. P., et al. (1991) Alzheimer's disease: paired helical filament immunoreactivity in cerebrospinal fluid. Acta Neuropathol 82:6–12.

What is claimed is:

1. A method for assessing a type of dementing disease in a patient suffering from a dementing disease, wherein said method comprises:

determining the concentration of heme oxygenase-1 (HO-1) and/or a nucleotide sequence encoding HO-1, in bodily fluid or non-neural tissue obtained from the patient; and comparing said concentration with the corresponding concentration of HO-1 and/or an HO-1 encoding nucleotide sequence in a corresponding bodily fluid or non-neural tissue obtained from at least one control person;

wherein a reduced concentration is used to predict the onset of, diagnose, or prognosticate an Alzheimer dementing disease; and wherein a concentration that is not reduced indicates that the dementing disease is not an Alzheimer dementing disease.

2. The method according to claim 1 wherein the concentration of HO-1 is determined and the bodily fluid is selected from plasma and cerebrospinal fluid and the tissue is selected from lymphocytes and fibroblasts, or the concentration of mRNA is determined and the tissue is selected from lymphocytes and fibroblasts.

3. A method for assessing dementing diseases in a patient which comprises:

determining the concentration of heme oxygenase-1 (HO-1), in plasma obtained from a patient; and comparing said concentration with the corresponding concentration of HO-1 in plasma obtained from at least one control person;

wherein such method is used to predict the onset of, diagnose, or prognosticate dementing diseases.

4. A method for assessing dementing diseases in a patient which comprises:

determining the concentration of heme oxygenase-1 (HO-1) in lymphocytes obtained from a patient; and comparing said concentration with the corresponding concentration of HO-1 in lymphocytes obtained from at least one control person;

wherein such method is used to predict the onset of, diagnose, or prognosticate dementing diseases.

5. A method for assessing dementing diseases in a patient which comprises:

determining the concentration of HO-1 mRNA in lymphocytes obtained from a patient; and comparing said concentration with the corresponding concentration of HO-1 mRNA in lymphocytes obtained from at least one control person;

wherein such method is used to predict the onset of, diagnose, or prognosticate dementing diseases.

6. The method of any one of claims 1 to 5 wherein the dementing disease is selected from the group consisting of Alzheimer's Disease, Age-Associated Cognitive Decline, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, Creutzfeld-Jacob disease, viral encephalitis and hypothyroidism.

7. The method of any one of claims 1 to 5 wherein the at least one control person is a normal age-matched person.

8. The method of any one of claims 1 to 5 wherein the at least one control person is the patient from whom the corresponding concentration of HO-1 and/or an HO-1 encoding nucleotide sequence in bodily fluid and tissue was obtained at an earlier date, and the method is used to prognosticate dementing diseases.

\* \* \* \* \*